(12) United States Patent
Amasino et al.

(10) Patent No.: US 7,129,396 B2
(45) Date of Patent: Oct. 31, 2006

(54) DOMINANT GENE DELAYING FLOWERING

(75) Inventors: Richard M Amasino, Madison, WI (US); Edward T Himelblau, Hampton Bays, NY (US); Scott D Michaels, Bloomington, IN (US); Si-Bum Sung, Madison, WI (US); Fritz M Schomburg, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 110 days.

(21) Appl. No.: 10/163,774

(22) Filed: Jun. 5, 2002

(65) Prior Publication Data

US 2003/0229924 A1 Dec. 11, 2003

(51) Int. Cl.
*C12N 15/29* (2006.01)
*C12N 15/82* (2006.01)
*A01H 5/00* (2006.01)

(52) U.S. Cl. ............... 800/298; 800/278; 435/320.1; 536/23.6

(58) Field of Classification Search .......... 536/23.1, 536/23.6; 800/298, 278, 290; 435/419, 435/468, 320.1
See application file for complete search history.

(56) References Cited

FOREIGN PATENT DOCUMENTS

WO WO 02/016655 A2 * 2/2002

OTHER PUBLICATIONS

Bowie et al, Science 247:1306-1310, 1990).*
McConnell et al, Nature 411 (6838):709-713, 2001.*
Kano-Murakami et al (1993, FEBS 334:365-368).*
Harper et al (Jan. 2003, Geneseq database, Derwent, Accession No. ABZ12646).*
Tadege et al (2003, Plant Biotechnology Journal 1(5):361-369).*
Lazar et al (1988, Mol. Cell. Biol. 8:1247-1252).*
Hill et al (1998, Biochem. Biophys. Res. Comm. 244:573-577).*
Guo et al (2004, Proc. Natl. Acad. Sci. USA 101:9205-9210).*
Clarke JH, Dean C. Mapping FRI, a locus controlling flowering time and vernalization response in *Arabidopsis thaliana*. Mol Gen Genet. 1994 242(1):81-9.
Koornneef M, Alonso-Blanco C, Peeters AJM, Soppe W. Genetic control of flowering time in *Arabidopsis*. Annu Rev Plant Physiol. Plant Mol. Biol. 1998 49:345-70.
Koornneef M, Blankestijn-de Vries H, Hanhart C, Soppe W, Peeters T. The phenotype of some late-flowering mutants is enhanced by a locus on chromosome 5 that is not effective in the Landsberg erecta wild-type. The Plant Journal. 1994 6(6):911-919.
Lee I, Michaels SD, Masshardt AS and Amasino RM. The late-flowing phenotype of Frigida and mutations in Luminidependens is suppressed in the Landsberg erecta strain of *Arabidopsis*. The Plant Journal. 1994 6(6):903-909.
Sandra SL, Amasino RM. Ecotype-Specific Expression of a Flowering Mutant Phenotype in *Arabidopsis thaliana*. Plant Physiol. 1996 111(2):641-644.
Weigel D. The genetics of flower development: from floral induction to ovule morphogenesis. Annu Rev Genet. 1995;29:19-39. Review.

* cited by examiner

*Primary Examiner*—Stuart F. Baum
(74) *Attorney, Agent, or Firm*—Quarles & Brady LLP

(57) ABSTRACT

The present invention discloses the function, the cDNA sequences, and the expressed amino acid sequences of two genes the expression of each of which delayed the flower initiation time of a plant. This information enables creation of transgenic plants with altered flower initiation time.

6 Claims, 1 Drawing Sheet

FIG 1

SEQUENCE LISTING

<160> NUMBER OF SEQ ID NOS: 6

<210> SEQ ID NO 1
<211> LENGTH: 1850
<212> TYPE: DNA
<213> ORGANISM: Arabidopsis
<220> FEATURE:
<221> NAME/KEY: intron -continued

<222> LOCATION: (97)..(596)

<400> SEQUENCE: 1

| | |
|---|---|
| atgaggagcg ttaataatag tagtgtcgac accgtgaacg ccgccgcttc cgccatcgtc | 60 |
| tccgctgagt ctagaacaca accgtcgtcg gttcaggtac ttctatgagc tcttttttt | 120 |
| ttttctgagt gaaaatgttt ttattttggt tcttttttt ttttttaaa gatcagtgtt | 180 |
| gttgctttga tttgccgacg tttctgacgg tgtatcgtga ttgtagtttt gattgctcag | 240 |
| agacatggtt tttataagta aaagtgagaa tttcgtgatg tttttgatgt tgatctgtt | 300 |
| tttgcaagtg ttacgtaacg aaattaaaca aagttttaag agattttgc gttacttatt | 360 |
| agttatgctc atttacctgt tattgcttta cttaactagg attaaagagt ttttgacgaa | 420 |
| agtagaaata taagaagatt cgagatttga acttatttta aatgtctatt atttatcagc | 480 |
| agcaccagag taggtgtggt ttcagcaaga tttaaacttc ttgataaagc tataagccat | 540 |
| tgaatcttta gctgatcact aatcttgttt ttattatgtc ctttgaattt caaagaaaa | 600 |
| aaagggaag ctggtggagc ttgtactggt gttttggatc caagaagaac aataaaagga | 660 |
| taggccacgc ggtgcttgta cccgaaccag ctgcatcagg agctgcggtg gctccagtcc | 720 |
| aaaactcttc gagcaattct acttcaatat tcatgccctt tatagctcct ccttcatctc | 780 |
| ctgcttcctt tctgccatca ggtcctccct ctgcgtcaca tactcctgat cctggtctac | 840 |
| tttgttccct aaccgtcaat gaaccgcctt cagcctttac tattggacca tacgctcatg | 900 |
| agactcaacc tgttactcct ccagtgttct ctgctttcac aacggaaccc tccaccgcgc | 960 |
| cattcacgcc acctcctgaa tcaccttctt cccctgaagt gccttttgct cagttactta | 1020 |
| catcttcatt ggaaagggct aggaggaaca gtggtggtgg aatgaatcag aagttttcag | 1080 |
| ctgcacacta cgagtttaag tcttgtcaag tgtatcctgg aagtccaggt ggtaatctaa | 1140 |
| tctctcctgg ttcaggtaca tcttctcctt acccagggaa atgctccatc atcgagtttc | 1200 |
| gtatcggcga acctccaaag tttcttggtt ttgagcactt cacagcgcgt aaatggggat | 1260 |
| caagattcgg ttctggatcc atcacacctg ctggacaagg ttcaaggttg ggttcaggtg | 1320 |
| cttttgactcc tgatggctca aagctaactt ctggtgtagt gacaccaaat ggtgcagaga | 1380 |
| ctgttataag aatgagttat gggaatctca caccacttga aggcagtctt ttggatagtc | 1440 |
| agatctctga ggttgcgtct ttagccaatt cggaccacgg gtcgtcaagg cataatgatg | 1500 |
| aagctctcgt ggttcctcac agagtttctt tcgagttgac tggtgaagac gttgcacggt | 1560 |
| gtcttgcaag caagctaaac cgttccggtt cacatgaaaa agcaagcggc gaacatttaa | 1620 |
| gaccaaactg ttgtaaaacg tcgggagaaa cagagagcga acagagtcag aagctaagat | 1680 |
| cgttttctac aggctctaac aaagaattca gtttgatag caccaatgaa gagatgatag | 1740 |
| agaaaattcg atcggagtgg tgggcgaatg agaaggtcgc cggaaaaggt gatcacagtc | 1800 |
| caagaaacag ttggactttc tttccagtct tacgctctgg acatacttag | 1850 |

<210> SEQ ID NO 2
<211> LENGTH: 1350
<212> TYPE: DNA
<213> ORGANISM: Arabidopsis
<220> FEATURE:
<221> NAME/KEY: CDS
<222> LOCATION: (1)..(1347)

<400> SEQUENCE: 2

| | |
|---|---|
| atg agg agc gtt aat aat agt agt gtc gac acc gtg aac gcc gcc gct<br>Met Arg Ser Val Asn Asn Ser Ser Val Asp Thr Val Asn Ala Ala Ala | 48 |

-continued

```
        1               5              10              15
tcc gcc atc gtc tcc gct gag tct aga aca caa ccg tcg tcg gtt cag     96
Ser Ala Ile Val Ser Ala Glu Ser Arg Thr Gln Pro Ser Ser Val Gln
             20              25              30 aaa aaa agg gga agc tgg tgg agc ttg tac tgg tgt ttt gga tcc aag    144
Lys Lys Arg Gly Ser Trp Trp Ser Leu Tyr Trp Cys Phe Gly Ser Lys
         35              40              45 aag aac aat aaa agg ata ggc cac gcg gtg ctt gta ccc gaa cca gct    192
Lys Asn Asn Lys Arg Ile Gly His Ala Val Leu Val Pro Glu Pro Ala
     50              55              60 gca tca gga gct gcg gtg gct cca gtc caa aac tct tcg agc aat tct    240
Ala Ser Gly Ala Ala Val Ala Pro Val Gln Asn Ser Ser Ser Asn Ser
 65              70              75              80 act tca ata ttc atg ccc ttt ata gct cct cct tca tct cct gct tcc    288
Thr Ser Ile Phe Met Pro Phe Ile Ala Pro Pro Ser Ser Pro Ala Ser
                 85              90              95 ttt ctg cca tca ggt cct ccc tct gcg tca cat act cct gat cct ggt    336
Phe Leu Pro Ser Gly Pro Pro Ser Ala Ser His Thr Pro Asp Pro Gly
             100             105             110 cta ctt tgt tcc cta acc gtc aat gaa ccg cct tca gcc ttt act att    384
Leu Leu Cys Ser Leu Thr Val Asn Glu Pro Pro Ser Ala Phe Thr Ile
         115             120             125 gga cca tac gct cat gag act caa cct gtt act cct cca gtg ttc tct    432
Gly Pro Tyr Ala His Glu Thr Gln Pro Val Thr Pro Pro Val Phe Ser
     130             135             140 gct ttc aca acg gaa ccc tcc acc gcg cca ttc acg cca cct cct gaa    480
Ala Phe Thr Thr Glu Pro Ser Thr Ala Pro Phe Thr Pro Pro Pro Glu
145             150             155             160 tca cct tct tcc cct gaa gtg cct ttt gct cag tta ctt aca tct tca    528
Ser Pro Ser Ser Pro Glu Val Pro Phe Ala Gln Leu Leu Thr Ser Ser
                 165             170             175 ttg gaa agg gct agg agg aac agt ggt ggt gga atg aat cag aag ttt    576
Leu Glu Arg Ala Arg Arg Asn Ser Gly Gly Gly Met Asn Gln Lys Phe
             180             185             190 tca gct gca cac tac gag ttt aag tct tgt caa gtg tat cct gga agt    624
Ser Ala Ala His Tyr Glu Phe Lys Ser Cys Gln Val Tyr Pro Gly Ser
         195             200             205 cca ggt ggt aat cta atc tct cct ggt tca ggt aca tct tct cct tac    672
Pro Gly Gly Asn Leu Ile Ser Pro Gly Ser Gly Thr Ser Ser Pro Tyr
     210             215             220 cca ggg aaa tgc tcc atc atc gag ttt cgt atc ggc gaa cct cca aag    720
Pro Gly Lys Cys Ser Ile Ile Glu Phe Arg Ile Gly Glu Pro Pro Lys
225             230             235             240 ttt ctt ggt ttt gag cac ttc aca gcg cgt aaa tgg gga tca aga ttc    768
Phe Leu Gly Phe Glu His Phe Thr Ala Arg Lys Trp Gly Ser Arg Phe
                 245             250             255 ggt tct gga tcc atc aca cct gct gga caa ggt tca agg ttg ggt tca    816
Gly Ser Gly Ser Ile Thr Pro Ala Gly Gln Gly Ser Arg Leu Gly Ser
             260             265             270 ggt gct ttg act cct gat ggc tca aag cta act tct ggt gta gtg aca    864
Gly Ala Leu Thr Pro Asp Gly Ser Lys Leu Thr Ser Gly Val Val Thr
         275             280             285 cca aat ggt gca gag act gtt ata aga atg agt tat ggg aat ctc aca    912
Pro Asn Gly Ala Glu Thr Val Ile Arg Met Ser Tyr Gly Asn Leu Thr
     290             295             300 cca ctt gaa ggc agt ctt ttg gat agt cag atc tct gag gtt gcg tct    960
Pro Leu Glu Gly Ser Leu Leu Asp Ser Gln Ile Ser Glu Val Ala Ser
305             310             315             320 tta gcc aat tcg gac cac ggg tcg tca agg cat aat gat gaa gct ctc   1008
```

```
Leu Ala Asn Ser Asp His Gly Ser Ser Arg His Asn Asp Glu Ala Leu
                325                 330                 335 gtg gtt cct cac aga gtt tct ttc gag ttg act ggt gaa gac gtt gca    1056
Val Val Pro His Arg Val Ser Phe Glu Leu Thr Gly Glu Asp Val Ala
            340                 345                 350 cgg tgt ctt gca agc aag cta aac cgt tcc ggt tca cat gaa aaa gca    1104
Arg Cys Leu Ala Ser Lys Leu Asn Arg Ser Gly Ser His Glu Lys Ala
                355                 360                 365 agc ggc gaa cat tta aga cca aac tgt tgt aaa acg tcg gga gaa aca    1152
Ser Gly Glu His Leu Arg Pro Asn Cys Cys Lys Thr Ser Gly Glu Thr
        370                 375                 380 gag agc gaa cag agt cag aag cta aga tcg ttt tct aca ggc tct aac    1200
Glu Ser Glu Gln Ser Gln Lys Leu Arg Ser Phe Ser Thr Gly Ser Asn
385                 390                 395                 400 aaa gaa ttc aag ttt gat agc acc aat gaa gag atg ata gag aaa att    1248
Lys Glu Phe Lys Phe Asp Ser Thr Asn Glu Glu Met Ile Glu Lys Ile
                405                 410                 415 cga tcg gag tgg tgg gcg aat gag aag gtc gcc gga aaa ggt gat cac    1296
Arg Ser Glu Trp Trp Ala Asn Glu Lys Val Ala Gly Lys Gly Asp His
                420                 425                 430 agt cca aga aac agt tgg act ttc ttt cca gtc tta cgc tct gga cat    1344
Ser Pro Arg Asn Ser Trp Thr Phe Phe Pro Val Leu Arg Ser Gly His
            435                 440                 445 act tag                                                             1350
Thr

<210> SEQ ID NO 3
<211> LENGTH: 449
<212> TYPE: PRT
<213> ORGANISM: Arabidopsis

<400> SEQUENCE: 3

Met Arg Ser Val Asn Asn Ser Val Asp Thr Val Asn Ala Ala Ala
1               5                   10                  15

Ser Ala Ile Val Ser Ala Glu Ser Arg Thr Gln Pro Ser Ser Val Gln
                20                  25                  30

Lys Lys Arg Gly Ser Trp Trp Ser Leu Tyr Trp Cys Phe Gly Ser Lys
            35                  40                  45

Lys Asn Asn Lys Arg Ile Gly His Ala Val Leu Val Pro Glu Pro Ala
        50                  55                  60

Ala Ser Gly Ala Ala Val Ala Pro Val Gln Asn Ser Ser Asn Ser
65                  70                  75                  80

Thr Ser Ile Phe Met Pro Phe Ile Ala Pro Pro Ser Ser Pro Ala Ser
                85                  90                  95

Phe Leu Pro Ser Gly Pro Pro Ser Ala Ser His Thr Pro Asp Pro Gly
            100                 105                 110

Leu Leu Cys Ser Leu Thr Val Asn Glu Pro Pro Ser Ala Phe Thr Ile
        115                 120                 125

Gly Pro Tyr Ala His Glu Thr Gln Pro Val Thr Pro Val Phe Ser
    130                 135                 140

Ala Phe Thr Thr Glu Pro Ser Thr Ala Pro Phe Thr Pro Pro Glu
145                 150                 155                 160

Ser Pro Ser Ser Pro Glu Val Pro Phe Ala Gln Leu Leu Thr Ser Ser
                165                 170                 175

Leu Glu Arg Ala Arg Arg Asn Ser Gly Gly Gly Met Asn Gln Lys Phe
            180                 185                 190

Ser Ala Ala His Tyr Glu Phe Lys Ser Cys Gln Val Tyr Pro Gly Ser
```

-continued

```
                195                 200                 205
Pro Gly Gly Asn Leu Ile Ser Pro Gly Ser Gly Thr Ser Ser Pro Tyr
    210                 215                 220

Pro Gly Lys Cys Ser Ile Ile Glu Phe Arg Ile Gly Glu Pro Pro Lys
225                 230                 235                 240

Phe Leu Gly Phe Glu His Phe Thr Ala Arg Lys Trp Gly Ser Arg Phe
                245                 250                 255

Gly Ser Gly Ser Ile Thr Pro Ala Gly Gln Gly Ser Arg Leu Gly Ser
            260                 265                 270

Gly Ala Leu Thr Pro Asp Gly Ser Lys Leu Thr Ser Gly Val Val Thr
        275                 280                 285

Pro Asn Gly Ala Glu Thr Val Ile Arg Met Ser Tyr Gly Asn Leu Thr
    290                 295                 300

Pro Leu Glu Gly Ser Leu Leu Asp Ser Gln Ile Ser Glu Val Ala Ser
305                 310                 315                 320

Leu Ala Asn Ser Asp His Gly Ser Ser Arg His Asn Asp Glu Ala Leu
                325                 330                 335

Val Val Pro His Arg Val Ser Phe Glu Leu Thr Gly Glu Asp Val Ala
            340                 345                 350

Arg Cys Leu Ala Ser Lys Leu Asn Arg Ser Gly Ser His Glu Lys Ala
        355                 360                 365

Ser Gly Glu His Leu Arg Pro Asn Cys Cys Lys Thr Ser Gly Glu Thr
    370                 375                 380

Glu Ser Glu Gln Ser Gln Lys Leu Arg Ser Phe Ser Thr Gly Ser Asn
385                 390                 395                 400

Lys Glu Phe Lys Phe Asp Ser Thr Asn Glu Glu Met Ile Glu Lys Ile
                405                 410                 415

Arg Ser Glu Trp Trp Ala Asn Glu Lys Val Ala Gly Lys Gly Asp His
            420                 425                 430

Ser Pro Arg Asn Ser Trp Thr Phe Phe Pro Val Leu Arg Ser Gly His
        435                 440                 445

Thr
```

<210> SEQ ID NO 4
<211> LENGTH: 1953
<212> TYPE: DNA
<213> ORGANISM: Arabidopsis
<220> FEATURE:
<221> NAME/KEY: intron
<222> LOCATION: (97)..(732)

<400> SEQUENCE: 4

```
atgaggaacg ttgttaataa cagcgttgag actgttaacg ccgccgctac cgccatcgtc    60
accgccgagt ctcgagtaca gccgtcttct tctcaggtaa actactaagc ttcttcttcc   120
agattttccg tgattgaaat gtgttttttct ctgctcata gatcagtatt gttacttgct   180
tgatttagat cgtgattccg agatttatag cttttgtttg aatgattgct ctgaaaattt   240
gatctgttct tagttttgaa tttcgcgatt ttgctgtttt gatttagctc atagttacga   300
aactgtagtg aatgtgattt gaatttgcga ttttggtgtt ttgatttga ttacgattct    360 agatcagagc taatggtgag cttagttctt gatttcacga ctttgatttg ttctctctgg   420
attacaattg tggtctcaaa aaggtaaaaa gatgcgttgt tgcttttttca atctttttgt   480 ggattggctt tacaagtcat aatagcatcc atgattaaaa aggttaaaag cgtttctatt   540
tcatgtttgg ttaattttcc acggatagta taaatttctc caaaagtgaa ttacaaacgt   600
```

-continued

```
ttagctactt attagaaact aaacaagatt aactttatta tcaaaagctt ttactttgag      660
aaagttttgt tgaaacagtt ctctctaaag gggatcaaga tgagtctaat tttgtgtgtt      720
taatttgtac agaagggaag atggggaaaa tgttggagtt tatattcatg ttttggaact      780
cagaagaaca ataaaaggat tggtaatgct gtgcttgtac ctgaaccggt tacatctgga      840
gttccggtag ttactgttca aaactcagct acttcaacta ctgttgttct tcccttata       900 gctcctcctt catctccagc ttcgttttg caatcggatc cttcatcggt ttctcactcg       960
cctgttggtc cactttctct tactagcaat acattctcgc taaggagcc tcaatctgtc      1020 tttaccgttg gaccttatgc taatgaaact caaccagtca ctcctccggt gttctctgcg     1080
tttataactg agccatctac tgcaccgtat actccacctc ctgaatcatc agtccatata     1140 actacaccctt cttcacctga agtgcccttt gctcagttgc ttacttcttc gttggagcta    1200
actcggaggg atagtactag tgggatgaat caaaagtttt cgtcttcgca ctatgagttt     1260
cggtctaatc aggtgtgtcc ggggagtcct ggtggtggta atctaatctc tcccgggtca    1320
gtgatttcaa actctggtac atcttctcct taccctggta aatcacccat ggttgagttt    1380
cgaataggcg agcctccaaa gttcttgggt tttgagcact ttacagctcg taaatgggga    1440
tcgaggttcg gttctggatc gatcacacct gttgggcatg gttcaggttt ggcttcaggc    1500
gctctgacac caaatggtcc agagatagta tctggaaact taacacccaa caataccaca   1560
tggcctcttc aaaatcagat ctctgaggtc gcttcactgg caaattcgga tcatggctct    1620
gaagtcatgg tagcagatca cagagtttcg tttgagttaa caggtgaaga cgttgcacgt   1680
tgtcttgcaa gcaagctaaa tcgatcacac gacagaatga acaacaatga ccggatcgaa   1740
acagaggaga gttcatcaac agacataaga agaaacatag agaaaggtc aggagacaga     1800 gagaacgaac agcatagaat tcagaagctg agttcctcat cgattggatc tagcaaagaa   1860
tttaaattcg acaacacgaa agacgagaat atcgagaagg ttgcaggaaa cagctggagt   1920
ttcttcccgg ggttacgatc tggagtcagc taa                                 1953
```

<210> SEQ ID NO 5
<211> LENGTH: 1317
<212> TYPE: DNA
<213> ORGANISM: Arabidopsis
<220> FEATURE:
<221> NAME/KEY: CDS
<222> LOCATION: (1)..(1314)

<400> SEQUENCE: 5

```
atg agg aac gtt gtt aat aac agc gtt gag act gtt aac gcc gcc gct      48
Met Arg Asn Val Val Asn Asn Ser Val Glu Thr Val Asn Ala Ala Ala
 1               5                  10                  15 acc gcc atc gtc acc gcc gag tct cga gta cag ccg tct tct tct cag      96
Thr Ala Ile Val Thr Ala Glu Ser Arg Val Gln Pro Ser Ser Ser Gln
             20                  25                  30 aag gga aga tgg gga aaa tgt tgg agt tta tat tca tgt ttt gga act     144
Lys Gly Arg Trp Gly Lys Cys Trp Ser Leu Tyr Ser Cys Phe Gly Thr
         35                  40                  45 cag aag aac aat aaa agg att ggt aat gct gtg ctt gta cct gaa ccg     192
Gln Lys Asn Asn Lys Arg Ile Gly Asn Ala Val Leu Val Pro Glu Pro
     50                  55                  60 gtt aca tct gga gtt ccg gta gtt act gtt caa aac tca gct act tca     240
Val Thr Ser Gly Val Pro Val Val Thr Val Gln Asn Ser Ala Thr Ser
 65                  70                  75                  80 act act gtt gtt ctt ccc ttt ata gct cct cct tca tct cca gct tcg     288
```

|   |   |
|---|---|
| Thr Thr Val Val Leu Pro Phe Ile Ala Pro Pro Ser Ser Pro Ala Ser<br>                85                      90                  95 |   |
| ttt ttg caa tcg gat cct tca tcg gtt tct cac tcg cct gtt ggt cca<br>Phe Leu Gln Ser Asp Pro Ser Ser Val Ser His Ser Pro Val Gly Pro<br>             100                    105                110 | 336 |
| ctt tct ctt act agc aat aca ttc tcg cct aag gag cct caa tct gtc<br>Leu Ser Leu Thr Ser Asn Thr Phe Ser Pro Lys Glu Pro Gln Ser Val<br>          115                    120                   125 | 384 |
| ttt acc gtt gga cct tat gct aat gaa act caa cca gtc act cct ccg<br>Phe Thr Val Gly Pro Tyr Ala Asn Glu Thr Gln Pro Val Thr Pro Pro<br>130                   135                    140 | 432 |
| gtg ttc tct gcg ttt ata act gag cca tct act gca ccg tat act cca<br>Val Phe Ser Ala Phe Ile Thr Glu Pro Ser Thr Ala Pro Tyr Thr Pro<br>145                   150                    155                160 | 480 |
| cct cct gaa tca tca gtc cat ata act aca cct tct tca cct gaa gtg<br>Pro Pro Glu Ser Ser Val His Ile Thr Thr Pro Ser Ser Pro Glu Val<br>                  165                   170                   175 | 528 |
| ccc ttt gct cag ttg ctt act tct tcg ttg gag cta act cgg agg gat<br>Pro Phe Ala Gln Leu Leu Thr Ser Ser Leu Glu Leu Thr Arg Arg Asp<br>                    180                   185                   190 | 576 |
| agt act agt ggg atg aat caa aag ttt tcg tct tcg cac tat gag ttt<br>Ser Thr Ser Gly Met Asn Gln Lys Phe Ser Ser Ser His Tyr Glu Phe<br>                  195                   200                   205 | 624 |
| cgg tct aat cag gtg tgt ccg ggg agt cct ggt ggt ggt aat cta atc<br>Arg Ser Asn Gln Val Cys Pro Gly Ser Pro Gly Gly Gly Asn Leu Ile<br>          210                    215                   220 | 672 |
| tct ccc ggg tca gtg att tca aac tct ggt aca tct tct cct tac cct<br>Ser Pro Gly Ser Val Ile Ser Asn Ser Gly Thr Ser Ser Pro Tyr Pro<br>225                   230                    235                240 | 720 |
| ggt aaa tca ccc atg gtt gag ttt cga ata ggc gag cct cca aag ttc<br>Gly Lys Ser Pro Met Val Glu Phe Arg Ile Gly Glu Pro Pro Lys Phe<br>                  245                   250                   255 | 768 |
| ttg ggt ttt gag cac ttt aca gct cgt aaa tgg gga tcg agg ttc ggt<br>Leu Gly Phe Glu His Phe Thr Ala Arg Lys Trp Gly Ser Arg Phe Gly<br>                  260                   265                   270 | 816 |
| tct gga tcg atc aca cct gtt ggg cat ggt tca ggt ttg gct tca ggc<br>Ser Gly Ser Ile Thr Pro Val Gly His Gly Ser Gly Leu Ala Ser Gly<br>                  275                   280                   285 | 864 |
| gct ctg aca cca aat ggt cca gag ata gta tct gga aac tta aca ccc<br>Ala Leu Thr Pro Asn Gly Pro Glu Ile Val Ser Gly Asn Leu Thr Pro<br>          290                    295                   300 | 912 |
| aac aat acc aca tgg cct ctt caa aat cag atc tct gag gtc gct tca<br>Asn Asn Thr Thr Trp Pro Leu Gln Asn Gln Ile Ser Glu Val Ala Ser<br>305                   310                    315                320 | 960 |
| ctg gca aat tcg gat cat ggc tct gaa gtc atg gta gca gat cac aga<br>Leu Ala Asn Ser Asp His Gly Ser Glu Val Met Val Ala Asp His Arg<br>                  325                   330                   335 | 1008 |
| gtt tcg ttt gag tta aca ggt gaa gac gtt gca cgt tgt ctt gca agc<br>Val Ser Phe Glu Leu Thr Gly Glu Asp Val Ala Arg Cys Leu Ala Ser<br>                    340                   345                   350 | 1056 |
| aag cta aat cga tca cac gac aga atg aac aac aat gac cgg atc gaa<br>Lys Leu Asn Arg Ser His Asp Arg Met Asn Asn Asn Asp Arg Ile Glu<br>          355                    360                   365 | 1104 |
| aca gag gag agt tca tca aca gac ata aga aga aac ata gag aaa agg<br>Thr Glu Glu Ser Ser Ser Thr Asp Ile Arg Arg Asn Ile Glu Lys Arg<br>          370                    375                   380 | 1152 |
| tca gga gac aga gag aac gaa cag cat aga att cag aag ctg agt tcc<br>Ser Gly Asp Arg Glu Asn Glu Gln His Arg Ile Gln Lys Leu Ser Ser<br>385                   390                    395                400 | 1200 |

-continued

| | | | | | | | | | | | | |
|---|---|---|---|---|---|---|---|---|---|---|---|---|
| tca | tcg | att | gga | tct | agc | aaa | gaa | ttt | aaa | ttc | gac | aac acg aaa gac | 1248 |
| Ser | Ser | Ile | Gly | Ser | Ser | Lys | Glu | Phe | Lys | Phe | Asp | Asn Thr Lys Asp |
| | | | 405 | | | | 410 | | | | | 415 |

| | | | | | | | | | | | | |
|---|---|---|---|---|---|---|---|---|---|---|---|---|
| gag | aat | atc | gag | aag | gtt | gca | gga | aac | agc | tgg | agt | ttc ttc ccg ggg | 1296 |
| Glu | Asn | Ile | Glu | Lys | Val | Ala | Gly | Asn | Ser | Trp | Ser | Phe Phe Pro Gly |
| | | 420 | | | | | 425 | | | | | 430 |

| | | | | | |
|---|---|---|---|---|---|
| tta | cga | tct | gga | gtc | agc taa | 1317 |
| Leu | Arg | Ser | Gly | Val | Ser |
| | | 435 | | | |

<210> SEQ ID NO 6
<211> LENGTH: 438
<212> TYPE: PRT
<213> ORGANISM: Arabidopsis

<400> SEQUENCE: 6

Met Arg Asn Val Val Asn Ser Val Glu Thr Val Asn Ala Ala Ala
1               5                   10                  15

Thr Ala Ile Val Thr Ala Glu Ser Arg Val Gln Pro Ser Ser Gln
            20                  25                  30

Lys Gly Arg Trp Gly Lys Cys Trp Ser Leu Tyr Ser Cys Phe Gly Thr
        35                  40                  45

Gln Lys Asn Asn Lys Arg Ile Gly Asn Ala Val Leu Val Pro Glu Pro
    50                  55                  60

Val Thr Ser Gly Val Pro Val Val Thr Val Gln Asn Ser Ala Thr Ser
65                  70                  75                  80

Thr Thr Val Val Leu Pro Phe Ile Ala Pro Pro Ser Ser Pro Ala Ser
                85                  90                  95

Phe Leu Gln Ser Asp Pro Ser Ser Val Ser His Ser Pro Val Gly Pro
            100                 105                 110

Leu Ser Leu Thr Ser Asn Thr Phe Ser Pro Lys Glu Pro Gln Ser Val
        115                 120                 125

Phe Thr Val Gly Pro Tyr Ala Asn Glu Thr Gln Pro Val Thr Pro Pro
    130                 135                 140

Val Phe Ser Ala Phe Ile Thr Glu Pro Ser Thr Ala Pro Tyr Thr Pro
145                 150                 155                 160

Pro Pro Glu Ser Ser Val His Ile Thr Thr Pro Ser Ser Pro Glu Val
                165                 170                 175

Pro Phe Ala Gln Leu Leu Thr Ser Ser Leu Glu Leu Thr Arg Arg Asp
            180                 185                 190

Ser Thr Ser Gly Met Asn Gln Lys Phe Ser Ser His Tyr Glu Phe
        195                 200                 205

Arg Ser Asn Gln Val Cys Pro Gly Ser Pro Gly Gly Asn Leu Ile
    210                 215                 220

Ser Pro Gly Ser Val Ile Ser Asn Ser Gly Thr Ser Ser Pro Tyr Pro
225                 230                 235                 240

Gly Lys Ser Pro Met Val Glu Phe Arg Ile Gly Glu Pro Pro Lys Phe
                245                 250                 255

Leu Gly Phe Glu His Phe Thr Ala Arg Lys Trp Gly Ser Arg Phe Gly
            260                 265                 270

Ser Gly Ser Ile Thr Pro Val Gly His Gly Ser Gly Leu Ala Ser Gly
        275                 280                 285

Ala Leu Thr Pro Asn Gly Pro Glu Ile Val Ser Gly Asn Leu Thr Pro
    290                 295                 300

Asn Asn Thr Thr Trp Pro Leu Gln Asn Gln Ile Ser Glu Val Ala Ser
305                 310                 315                 320

```
Leu Ala Asn Ser Asp His Gly Ser Glu Val Met Val Ala Asp His Arg
            325                 330                 335

Val Ser Phe Glu Leu Thr Gly Glu Asp Val Ala Arg Cys Leu Ala Ser
            340                 345                 350

Lys Leu Asn Arg Ser His Asp Arg Met Asn Asn Asn Asp Arg Ile Glu
            355                 360                 365

Thr Glu Glu Ser Ser Ser Thr Asp Ile Arg Arg Asn Ile Glu Lys Arg
        370                 375                 380

Ser Gly Asp Arg Glu Asn Glu Gln His Arg Ile Gln Lys Leu Ser Ser
385                 390                 395                 400

Ser Ser Ile Gly Ser Ser Lys Glu Phe Lys Phe Asp Asn Thr Lys Asp
            405                 410                 415

Glu Asn Ile Glu Lys Val Ala Gly Asn Ser Trp Ser Phe Phe Pro Gly
            420                 425                 430

Leu Arg Ser Gly Val Ser
            435
```

DOMINANT GENE DELAYING FLOWERING

STATEMENT REGARDING FEDERALLY SPONSORED RESEARCH OR DEVELOPMENT

This invention was made with United States government support awarded by the following agency: DOE DE-FC05-920R22072. The United States has certain rights in this invention.

CROSS-REFERENCE TO RELATED APPLICATIONS

Not applicable.

BACKGROUND OF THE INVENTION

The transition of growing plants from vegetative growth to flowering is the major developmental switch in the plant life cycle. The timing of flower initiation is critical for the reproductive success of wild plants, and most plant species have evolved systems to precisely regulate flowering time. These systems monitor both environmental cues and the developmental state of the plant to control flowering.

Two commonly monitored environmental cues are photoperiod and temperature. In the photoperiod-responsive plants so examined, daylength is perceived in leaves and flowering signals appear to be translocated from leaves to meristems (Zeevaart, Light and the Flowering Process, Process, eds., D. Vince-Prue, B. Thomas and K. E. Cockshull, 137–142, Academic Press, Orlando, 1984.). Exposure to cold temperatures promotes flowering by a process known as vernalization. Vernalization affects meristems directly, perhaps by causing them to become competent to perceive flowering signals (Lang, Encyclopedia of Plant Physiology, ed., W. Ruhland, 15 (Part 1), 1371–1536, Springer-Verlag, Berlin, 1965). Other environmental cues that can affect flowering include light quality and nutritional status.

The developmental state of the plant can also influence flowering time. Most species go through a juvenile phase during which flowering is suppressed, and eventually undergo a transition to an adult phase in which the plant is competent to flower (Poethig, Science, 250, 923–930, 1990). This "phase change" permits the plant to reach a proper size for productive flowering.

In the flowering literature, the developmental flowering pathways are often referred to as autonomous to indicate that they do not involve the sensing of photoperiod. However, it is unlikely that autonomous and photoperiod pathways are entirely distinct. For example, day-neutral species of tobacco flower after producing a specific number of nodes and thus could be classified as flowering entirely through an autonomous pathway, but grafting studies indicate that day-neutral and photoperiod-responsive tobacco species respond to similar translocatable flowering signals (Lang et al., Proc. Natl. Acad. Sci., USA, 74, 2412–2416, 1977; McDaniel et al., Plant J., 9, 55–61, 1996). Thus aspects of the underlying biochemistry of these pathways appear to be conserved.

Genetic analyses in several species has identified genes that affect the timing of flowering. The most extensive genetic analysis of flowering-time genes has been performed in *Arabidopsis thaliana*. In Arabidopsis, flowering-time genes have been identified by two approaches. One approach has been to induce mutations that affect flowering time in early-flowering varieties. Such mutations can cause either late-flowering or even earlier flowering. Late-flowering mutations identify genes whose wild-type role is to promote flowering and early-flowering mutations identify inhibitory ones. Studies in Arabidopsis have identified over 20 loci for which mutations specifically affect flowering time and several other loci that affect flowering time as well as other aspects of development (e.g., det2, cop1, ga1 and phyB) (Koornneef et al., Ann. Rev. Plant Physiol., Plant Mol. Biol., 49, 345–370, 1998; Weigel, Ann. Rev. Genetics, 29, 19–39, 1995).

Another approach to identify flowering-time genes is to determine the genetic basis of naturally occurring variation in flowering time. Although the varieties of Arabidopsis most commonly used in the laboratory are early-flowering (summer annuals), most varieties are late-flowering (winter annuals). Late-flowering varieties differ from early-flowering ones in that the late-flowering varieties contain dominant alelles at two loci, FRIGIDA (FRI) and FLOWERING LOCUS C (FLC) that suppress flowering (Sanda et al., Plant Physiol., 111, 641–645, 1996; Lee et al., Plant Journal, 6, 903–909, 1994; Clarke et al., Mol. Gen. Genet., 242, 81–89, 1994; Koornneef et al., Plant Journal, 6, 911–919, 1994).

Physiological analyses of flowering-time mutants and naturally occurring variation in flowering time indicate that flowering is controlled by multiple pathways in Arabidopsis (Koornneef et al., Ann. Rev. Plant Physiol., Plant Mol. Biol., 49, 345–370, 1998). One group of late-flowering mutants (fca, fpa, fve, fy, ld) and plants containing the late-flowering FLC and FRI alleles are delayed in flowering in inductive (long-day) conditions and are even more severely delayed in short days. Vernalization of these late-flowering lines can suppress the late-flowering phenotype. Another group of late-flowering mutants (co, fd, fe, fha, ft, fwa, gi) exhibit a slight or no difference in flowering time when grown in short days compared to long days. Furthermore, this group shows little or no response to vernalization. Double mutants within a group do not flower significantly later than either single-mutant parent, whereas double mutants containing a mutation in each group flower later than the single-mutant parents (Koornneef et al., Genetics, 148, 885–92, 1998). Thus, there appears to be parallel flowering pathways that mediate the flowering response to environmental and developmental cues. A photoperiod pathway promotes flowering in long days. A pathway referred to in the literature as autonomous appears to control the age, or more specifically the developmental stage, at which plants are competent to flower. Recent support of the developmental role of this pathway is the demonstration that autonomous pathway mutants exhibit changes such as alterations of trichome patterns that indicate such mutant plants are delayed in the juvenile to adult transition (Telfer et al., Development, 124, 645–654, 1997).

Blocks to the autonomous pathway due to mutant fca, fpa, fve, fy, and ld alleles or to the presence of dominant late-flowering FLC and FRI alleles can be bypassed by vernalization (Koornneef et al., Ann. Rev. Plant Physiol., Plant Mol. Biol., 49, 345–370, 1998). Thus FLC and FRI can be regarded as genes that create a requirement for vernalization. Other species, particularly Brassicas, appear to have the same "circuitry" as Arabidopsis. This similarity has been most thoroughly analyzed for the relationship between dominant suppressors of flowering and vernalization in Brassicas. The major difference between annual and biennial cultivars of oilseed *Brassica napus* and *B. rapa* is conferred by genes controlling vernalization-responsive flowering time (Osborn et al., Genetics Society of America, 146, 1123–1129, 1997). By comparing quantitative trait loci (QTLs) in segregating populations of annual X biennial varieties of *B. rapa* and *B. napus*, it was shown that the 2 major QTLs that confer vernalization-responsive late flowering in *B. napus* and *B. rapa* are likely to be the same (Osborn et al., Genetics Society of America, 146, 1123–1129, 1997). In *B. rapa* the two flowering-time QTLs were separated in recombinant inbred populations and the QTL with the greatest effect on flowering time was VFR2 (vernalization-responsive flowering time in rapa 2). Furthermore, VFR2 appears to correspond to FLC from Arabidopsis: VFR2 was mapped at high resolution using hybridization probes that permit a comparison of Arabidopsis and Brassicas after introgression of the late allele into the early-flowering annual variety, and only a probe corresponding to FLC detected no recombination events with VFR2 (<0.44 cm) indicating that VFR2 is an FLC homolog.

The timing of flowering is of great importance in both agricultural and horticultural crops. In horticultural crops the product is often the flowers. In food, feed crops, or fiber crops, such as the cereals rice, wheat, maize, barley, oats, soybeans, canola, cotton, sunflower, tomato, and broccoli, the product is often the flower or the result of flowering—fruits, seeds, or seedpods. Identifying new genes that are involved in flowering-time control will lead to new strategies to optimize flower, fruit, and seed production by genetic manipulations. For example, in certain crops accelerating the onset of flowering would permit the crops to be grown in a region where the growing season is otherwise too short, or permit multiple crops in a region where only one crop is currently possible.

There are also crops in which the non-flowering parts of the plant are the useful parts. In such crops preventing or substantially delaying flowering will increase the yield of these useful parts. Examples of plants in which delaying or preventing flowering would be desirable include forage crops such as alfalfa and clover, and vegetables such as cabbage and related Brassicas, spinach and lettuce. In crops in which underground parts are used, such as sugar beet or potato, delaying or preventing flowering should increase yield. Also, in sugar beet, prevention of flowering will permit more energy to be devoted to sugar production. Likewise the yield of wood and biomass crops will be increased by delaying flowering. Identifying new genes that are involved in flowering time control will provide new tools to delay flowering in the above plants.

BRIEF SUMMARY OF THE INVENTION

The present invention discloses the function, the cDNA sequences, and the expressed amino acid sequences of two genes that are involved in flowering repression. The present invention includes various nucleic acid molecules and polypeptides that are related to the gene and useful in various applications such as detecting the gene, generating antibodies to the product of the gene, and generating plants with altered flower initiation time. The present invention also includes various host cells containing the nucleic acid molecules. The present invention also includes methods of generating plants with altered flower initiation time using the nucleic acid molecules and the polypeptides described above, the resulted plants and parts thereof, and progeny, variants and mutants of the plants and parts thereof.

It is an object of the present invention to provide a tool to creators of new plant varieties to alter the flower initiation time of a plant. The flower initiation time can be made earlier or later.

It is an advantage of the present invention that both genes is dominant with regard to the delayed flower initiation time phenotype so that a transgenic plant with delayed flower initiation time is easy to create.

Other objects, advantages and features of the present invention will become apparent from the following specifications and claims.

BRIEF DESCRIPTION OF THE SEVERAL VIEWS OF THE DRAWINGS

FIG. 1 shows alignment of VIN4 and VIN4-relative proteins.

DETAILED DESCRIPTION OF THE INVENTION

Set forth below are the cDNA (SEQ ID NO:2 and SEQ ID NO:5) and the deduced amino acid (SEQ ID NO:3 and SEQ ID NO:6) sequences of two Arabidopsis late flowering genes, here named VIN4 and VIN4-relative, respectively. It is disclosed here that an increase in VIN4 or VIN4-relative activity in plants causes a delay in flower initiation, while a decrease of VIN4 or VIN4-relative activity in plants causes an advance in flower initiation. Prior to the present invention, the genomic DNA sequences (SEQ ID NO:1 and SEQ ID NO:4), but not the cDNA sequences, the amino acid sequences and the function, of these two genes were known. The present invention provides plant breeders and creators a unique tool so as to sculpt the flower initiation time of a plant to more closely follow the desires of the breeder. The plants whose flower initiation time can be altered in the present invention include those whose flowering is responsive to photoperiod, temperature, developmental stage or other factors.

Figure 1:
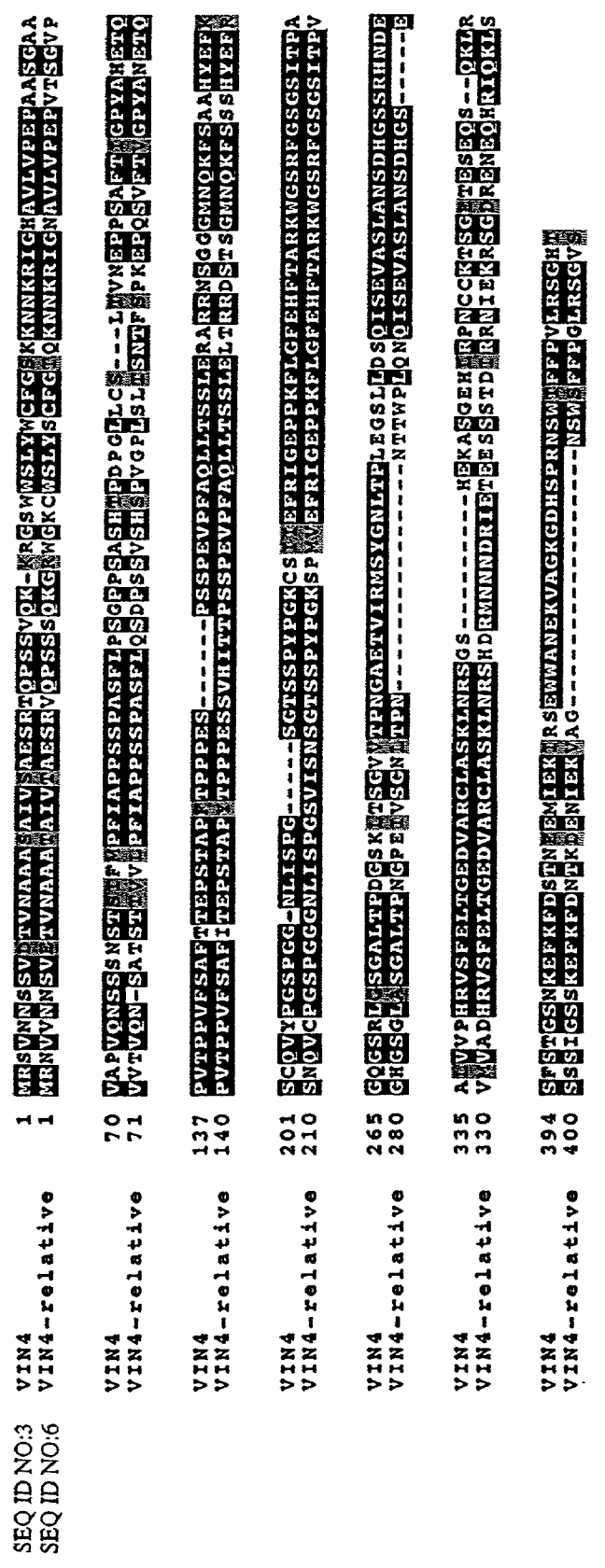

A lineup of VIN4 and VIN4-relative protein amino acid sequences (FIG. 1) shows that they are 63% identical. A search of Genbank did not reveal any genes from other plant species or other organisms that are similar. A search in the recently released Chinese rice database did not reveal any match either.

In one aspect, the present invention relates to a polypeptide including an amino acid sequence that has at least 35%, 40%, 50%, 60%, 70%, 80%, 90%, 95%, 97%, or 99% identity to and over the entire length of that of SEQ ID NO:3, SEQ ID NO:6, SEQ ID NO:3 with conservative substitutions, or SEQ ID NO:6 with conservative substitutions. The present invention also relates to a polypeptide including a novel fragment of the amino acid sequence described above, especially a fragment that is immunogenic or has a biological activity of either delaying or advancing the flower initiation time of a plant. Besides the amino acid sequence described above, the polypeptide of the present invention can include a native or non-native amino acid sequence at the N- or C-terminus or both, which will not interfere with the function of the amino acid sequence described above. The flanking native or non-native amino acid sequence can but does not have to be one that assists in purification, detection, or stabilization of the amino acid sequence described above.

As used herein, "percent identity" of the two amino acid sequences or of two nucleic acids is synonymous to "percent homology," which is determined using the algorithm of Karlin and Altschul (Proc. Nati. Acad. Sci. USA 87:2264–2268, 1990), modified as in Karlin and Altschul (Proc. Nati. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:3). To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used.

Also within the scope of the present invention are polypeptides that bind specifically to an antibody that binds specifically to the VIN4 protein or the VIN4-relative protein.

In another aspect, the present invention relates to isolated nucleic acid molecules as described below. An "isolated nucleic acid molecule" used herein is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecules but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library. An isolated nucleic acid molecule can be modified or unmodified DNA or RNA, whether fully or partially single-stranded or double-stranded or even triple-stranded. A modified nucleic acid molecule can be chemically or enzymatically induced and can include so-called non-standard bases such as inosine.

An isolated nucleic acid molecule of the present invention is one that includes a polynucleotide having an uninterrupted coding sequence that encodes a polypeptide the amino acid sequence of which is at least 35%, 40%, 50%, 60%, 70%, 80%, 90%, 95%, 97%, or 99% identical to SEQ ID NO:3 or SEQ ID NO:6, a complement of the foregoing, or a novel fragment of any of the foregoing. A preferred nucleic acid molecule includes a polynucleotide having a sequence that is at least 35%, 40%, 50%, 60%, 70%, 80%, 90%, 95%, 97% or 99% identical to SEQ ID NO:2 or SEQ ID NO:5.

The invention also includes nucleic acid molecules that hybridize under stringent hybridization conditions (as defined herein) to all or a portion of the nucleotide sequence represented by SEQ ID NO:2 or its complement, or SEQ ID NO:5 or its complement. The hybridizing portion of the hybridizing nucleic acid molecules is typically at least 15 (e.g., 20, 25, 30, or 50) nucleotides in length. The hybridizing portion of the hybridizing nucleic acid molecules is at least 80%, e.g., at least 95%, or at least 99%, identical to the sequence of a portion or all of a nucleic acid encoding a VIN4 or VIN4-relative polypeptide, or the sequence's complement. Hybridizing nucleic acid molecules of the type described herein can be used, for example, as a cloning probe, a primer (e.g., a PCR primer), or a diagnostic probe. Hybridization of the oligonucleotide probe to a nucleic acid sample typically is performed under stringent conditions.

Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5× Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Isolated nucleic acid molecules of the invention can be obtained by several methods. For example, they can be isolated using procedures which are well known in the art. These include, but are not limited to: (a) hybridization of detectably labeled probes representing all or part of the VIN4 or VIN4-relative gene to genomic or cDNA libraries to detect similar nucleic acid sequences; (b) antibody screening of expression libraries to detect similar structural features; (c) synthesis by the polymerase chain reaction (PCR); and (d) chemical synthesis of a nucleic acid molecule. Sequences for specific coding regions of genes can also be found in GenBank, the National Institutes of Health computer database.

For the identification of isolated nucleic acid molecules using detectably labeled probes, or for the identification of polynucleotide fragments whose complements hybridize to VIN4 or VIN4-relative, stringent hybridizing conditions described above can be used. Alternatively, higher stringency conditions can be used. Typically, lower stringency hybridization conditions permit hybridization of the probes to polynucleotides related but not identical to the VIN4 or VIN4-relative gene, and thereby allow identification of VIN4 or VIN4-relative genes in other species.

In a related aspect, any polynucleotide of the present invention including those that can be used as antisense polynucleotides can be provided in a vector or genetic construct in a manner known to those skilled in the art. A polypeptide-encoding polynucleotide or an antisense fragment thereof so provided in a vector can, but need not, be under the transcriptional control of one or more regulatory elements which can include a promoter not natively found adjacent to the polynucleotide such that the encoded polypeptide can be produced when the vector is provided in a compatible host cell or in a cell-free transcription and translation system. Such cell-based and cell-free systems are well known to the skilled artisan. Cells comprising a vector containing a polynucleotide of the invention are themselves within the scope of the invention.

In another related aspect, the present invention encompass a polynucleotide having a nucleotide sequence that encodes a polypeptide the amino acid sequence of which is at least 35%, 40%, 50%, 60%, 70%, 80%, 90%, 95%, 97%, or 99% identical to SEQ ID NO:3 or SEQ ID NO:6, operably linked to a non-native expression control sequence which can include a promoter. Such a polynucleotide of the present invention can be provided in a vector such that the encoded polypeptide can be produced when the vector is provided in a compatible host cell or in a cell-free transcription and translation system. Such cell-based and cell-free systems are well known to the skilled artisan. Cells comprising the vector are themselves within the scope of the invention.

In yet another aspect, the present invention relates to a method of altering the flower initiation time of a plant and the resulted plant. The normal function of VIN4 and VIN4-relative is to delay or inhibit flowering. However, the availability of the genetic sequences of the VIN4 gene and the VIN4-relative gene enable the flower initiation time of a plant to be altered in either direction. Increasing and decreasing the activity of VIN4 or VIN4-relative will cause a delay and an advance in flower initiation timing, respectively.

Several techniques are now known to be practical to either increase or decrease the activity of VIN4 or VIN4-relative. One way to increase the activity of VIN4 or VIN4-relative is to increase the transcription or translation rate, or the stability of the mRNA or protein products of VIN4 or VIN4-relative. Another way to increase the activity of VIN4 or VIN4-relative in a plant is to introduce into the plant and express a VIN4 or VIN4-relative gene (either the genomic DNA or cDNA) of the same or a different species, a portion of a VIN4 or VIN4-relative gene the protein product of which retains the function of delaying flower initiation, or other nucleic acid molecules of the present invention that are effective when expressed in a plant to cause a delay in the flower initiation time in the plant as compared to a plant of the same genetic background without the transgene. The term transgene is here used to apply to an inserted nucleic acid carried in the cells of a target plant. A plant that carries such a transgene is referred to as a transgenic plant.

When the plant in which a copy of a VIN4 gene, a VIN4-relative gene or another nucleic acid of the present invention is introduced also contains a wild-type flower time regulation coding region which acts to repress flower initiation, the introduction into the genome of the plant the VIN4 gene, the VIN4-relative gene or the other nucleic acid of the present invention can act to augment the activity of the endogenous flower time regulation coding region to make flower initiation occur later.

The examples below showed that expressing the Arabidopsis VIN4 or VIN4-relative gene introduced into an Arabidopsis plant delayed the flower initiation time of the plant. Identical or similar techniques can be used to express a VIN4 or VIN4-relative gene in other plant species to delay the flower initiation time of those species. In addition, this Arabidopsis system can be used to test possible VIN4 or VIN4-relative genes from other plant species and those nucleic acid molecules of the present invention that are effective to cause a delay in flower initiation in the transgenic plant as compared to a non-transgenic plant of the same genetic background.

There are many ways to decrease the activity of VIN4 or VIN4-relative in a plant. One way to decrease the activity of VIN4 or VIN4-relative is through the use of antisense technology, in which a genetic construct is created which causes the synthesis in the cells of the plant of an mRNA strand complementary to some portion of the mRNA created during the expression of a target gene (Bariola et al., Plant Physiol., 119, 331–342 (1999); Kang et al., Plant Mol. Biol., 38, 1021–1029, 1998). The antisense RNA interferes with the translation of the target mRNA and less protein is produced in the affected plant cells. A construct producing an antisense RNA would generally include a promoter driving the production of an antisense RNA polynucleotide molecule complementary to an mRNA produced by the target gene. In the present invention, the antisense RNA can include a polynucleotide sequence that is complementary to a portion of the corresponding VIN4 or VIN4-relative mRNA.

Another method to decrease the activity of VIN4 or VIN4-relative is to use cosuppression. Cosuppression is a poorly understood phenomenon by which insertion of an artificial gene construct into a plant occasionally causes suppression of both the inserted gene and any other gene homologous to it. In general, a cosuppression construct will raise the level of VIN4 or VIN4-relative mRNA, or a fragment of the mRNA, to a level that the cell will decrease expression of both the endogenous VIN4 or VIN4-relative gene and the transgene (Kasschau et al., Cell, 95, 461–470, 1998). Cosuppression can occur by introducing a VIN4 or VIN4-relative polynucleotide fragment that includes a VIN4 or VIN4-relative coding region, or portion thereof, which is identical to the endogenous VIN4 or VIN4-relative coding region.

Another method to decrease the activity of VIN4 or VIN4-relative is to introduce into a plant genome a polynucleotide fragment that encodes a polypeptide that would bind to the VIN4 or VIN4-relative gene, or its RNA, or a protein encoded by the VIN4 or VIN4-relative gene and render it inactive or less active.

Another method to decrease the activity of VIN4 or VIN4-relative is to introduce into a plant genome polynucleotide encoding dominant-negative versions of the endogenous VIN4 or VIN4-relative protein. Dominant-negative mutants are proteins that actively interfere with the function of normal, endogenous proteins. Thus, the action of a gene can be blocked without inactivating the structural gene itself or its RNA. Dominant-negative VIN4 and VIN4-relative polypeptides can be identified by modifying wild-type VIN4 and VIN4-relative and then determining the mutants' dominant-negative activity.

It should be understood that techniques of plant genetic engineering have been developed to the point where it is now practical to place any genetic construct into almost any useful plant species. The process does, however, still involve some random processes, most notably that insertions of foreign DNA into the genome of plants still occurs at random sites in the plant genome. As a result, in any group of plants emerging from a plant transformation process, the results achieved for the different gene insertion events will vary, sometimes dramatically. For example, for a simple gene insertion of another copy of an endogenous plant gene, many plants produced will have a slightly higher level of activity of the endogenous protein, others will have no measurable change or even a decrease in measurable activity, while a few will have substantial increases in activity levels. However, this variation does not mean stable results cannot be achieved, since the results tend to be consistent generation-to-generation for each specific genetic insertion. Thus the high activity plants have, in effect, a high activity allele that can be transferred by normal Mendelian inheritance to their progeny. One can also take advantage of this variation to generate lines with broad range of flowering time (see Table 2 below).

To make a transgenic plant, as is known to those of skill in the art, one needs to make a genetic construction capable of expressing an inserted protein coding sequence, whether foreign or endogenous, in a plant. One also needs a method to insert the genetic construction into the plant.

The tools and techniques for making genetic constructions that will express proteins in plants are now widely known. Any genetic construction intended to cause the synthesis in the cells of the plant of a polypeptide or protein must include a sequence of DNA known as a protein coding sequence (can be a genomic DNA or a cDNA), which specifies the sequence of the polypeptide or protein to be produced in the resultant plant. For a protein coding sequence to be expressed in a plant to produce a polypeptide or protein, it must be placed under the control of a plant expressible promoter and be followed by a plant transcriptional terminator sequence, also known as a polyadenlyation sequence. The plant expressible promoter is a promoter which will work in plants, usually either of plant origin or from a plant pathogen like a virus (e.g. Cauliflower mosaic virus) or a bacteria (e.g. Agrobacterium promoters like the nopaline synthase promoter).

Plant promoters from pathogens tend to be constitutive promoters, meaning that they actually express the protein coding sequence in all of the tissues of the plant at all times. Examples of constitutive promoters useful in plant genetic constructions include, without limitation, the 35S RNA and 19S RNA promoters of the Cauliflower mosaic virus (Brisson et al., Nature, 310, 511, 1984), and the opine synthase promoters carried on the tumor-inducing plasmids of *Agrobacterium tumefaciens* such as the nopaline synthase promoter (Ebert et al., PNAS, 84, 5745, 1987) and the mannopine synthase promoter (Velten et al., EMBO J. 3, 2723 1984).

Other plant promoters are known to be tissue specific (e.g. to flower) or developmentally specific (e.g. to stage of plant life such as emergent specific or senescent specific), while others are intended to be inducible (e.g. heat shock or metal ion induced promoters). An example of a tissue-specific promoter is the H4A748 promoter expressed in shoot meristems (Atanassova et al., Plant J., 2, 291, 1992. Examples of inducible promoters suitable for use in the present invention include, but are not limited to, heat shock promoters such as soybean hsp17.5E or hsp17.3 (Gurley et al., Mol. Cell Biol. 6, 559, 1986), light-regulated promoters such as the promoter for the small subunit or ribulose bisphosphate carboxylase (ssRUBISCO) (Coruzzi et al., EMBO J. 3, 1671, 1984; Broglie et al., Science 224, 838, 1984), chemical-regulated promoters such as Maize In2–1 and 2–2 which are regulated by benzenesulfonamides, e.g., herbicide safeners (Hershey et al., Plant Mol. Biol., 17, 679, 1991), and alcA and alcR promoter/transcription factor system that is induced by the application of ethanol (Caddick et al., Nat. Biotech., 16, 177, 1998). Other promoters of gene expression will be known to those skilled in the art.

Any of the promoters described above may be used in the practice of this invention depending on the intended effect on the transgenic plant to be produced. For example, a plant with its flowering delayed for a specific time period may be obtained through adjusting the expression level of a transgene by varying promoter strength.

Optionally, a selectable marker may be associated with a genetic construct used to generate a transgenic plant. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase, and amino-glycoside 3'-O-phosphotransferase II (which confers kanamycin, neomycin and G418 resistance). Other suitable markers will be known to those of skill in the art.

The genetic constructs described above for expressing a coding sequence applies to expressing an antisense or cosuppression polynucleotide as well.

Several methods have been demonstrated to insert genes into plants to make them transgenic. The most widely used methods, broadly defined, are Agrobacterium-mediated transformation and accelerated particle mediated transformation. The various techniques of Agrobacterium-mediated plant transformation make use of the natural ability of the plant pathogens of the Agrobacterium genus to transfer DNA from a plasmid in the bacteria into the genome of a plant cell. Particle-mediated plant transformation techniques utilize DNA-coated small carrier particles accelerated from a device, often referred to as a gene gun, into the cells of a plant. The full implementation of either approach requires techniques to recover a fully mature, morphologically normal plant from the transformed cells. The techniques often therefore involve either selection or screening protocols to identify which plant cell was transformed and regeneration protocols to recover a whole plant from a single transformed plant cell. As mentioned above, these techniques have been worked out for many plant species and many, and perhaps all, of the economically important plant species.

Viruses such as the Cauliflower mosaic virus (CaMV) may also be used as a vector for introducing a transgene into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid again may be cloned and further modified by introduction of the desired polynucleotide sequence. The modified viral portion of the recombinant plasmid is then excised from the parent bacterial plasmid, and used to inoculate the plant cells or plants.

Other techniques, such as electroporation have also been used to make transgenic plants. But fundamentally for the invention disclosed here, the particular technique of plant transformation does not matter. Once the plant has been genetically engineered, and a transgenic plant has been created, the method of transformation of the original plant becomes irrelevant. A transgene inserted into the genome of one plant is then fully inheritable by progeny plants of the original genetically engineered plant by normal rules of classical plant breeding. For example, in vegetatively propagated crops, the mature transgenic plants are propagated by the taking of cuttings or by tissue culture techniques to produce multiple identical plants. Selection of desirable transformed plants is made and new varieties are obtained and propagated vegetatively for commercial use. In seed-propagated crops, the mature transgenic plants can be self crossed to produce a homozygous inbred plant. The inbred plant produces seed containing the newly introduced transgene. These seeds can be grown to produce plants that would produce the selected phenotype, modified timing of flower initiation.

The transgenic plants created by the methods described above, which have the phenotypic trait of altered flower initiation time relative to the same plants without the transgene inserted, are within the scope of the present invention.

Progeny, variants, and mutants of these plants are also within the scope of the invention, provided that they comprise the introduced transgene. Parts obtained from the plants of the present invention, such as flowers, seeds, leaves, branches, fruits, and the like are included in the invention, provided that these parts comprise cells that contain the transgene.

The lifetime of a plant can be divided into at least two phases, the vegetative phase and the reproductive phase. In most commercially important crop plants, during the vegetative phase the plant continues growth, which includes increasing in size and in the number of leaves present on the plant. The reproductive phase begins with flower initiation. At that point much of the plant's further growth is the growth (or development) of flowers, fruits, and seeds. Commercially important crop plants have been bred for desirable characteristics, including uniformity in the time the plants are ready for harvesting. This has resulted in a high degree of uniformity in the number of leaves present on each plant in a population of plants grown under the same conditions. Due to the uniformity in the number of leaves present, alterations in the flower initiation time can often be measured as a function of the number of leaves on a plant. For instance, if flower initiation is activated early in a plant, that plant will have fewer leaves relative to the same plant grown under the same conditions that do not activate flower initiation early. Moreover, a plant that activates flower initiation early can also be said to have a shortened vegetative phase relative to the same plant grown under the same conditions that do not activate flower initiation early. Likewise, if flower initiation is repressed such that the plant undergoes flower initiation later, that plant will have more leaves relative to the same plant grown under the same conditions that do not repress flower initiation until later. Moreover, a plant that represses flower initiation may also be said to have a prolonged vegetative phase relative to the same plant grown under the same conditions that do not repress flower initiation. Alterations in the time of flower initiation can also be measured as a function of time.

Preferably, the flower initiation time (on average) in the transgenic plant of the present invention is delayed for at least about 7 to 14 days, more preferably at least about 15 to 30 days, most preferably at least about 31 to 130 days than that of the same plant without the transgene. Alternatively, the flower initiation time (on average) in the transgenic plant is advanced for at least about 3 days, more preferably at least about 7 days, most preferably at least about 12 days than that of the same plant without the transgene. Preferably, the genetically modified plant and the same plant without the transgene are grown under the same conditions.

The different length of time to the onset of the flowering stage of the plant relative to the same plant without the transgene can also be measured by determining the difference in the number of leaves on the genetically modified plant at the flower initiation time and the number of leaves on the same plant without the transgene at the flower initiation time. Preferably, the transgenic plant of the present invention exhibits at least about 20% more, more preferably at least about 100% more, most preferably at least about 200% more leaves at the flower initiation time than the same plant without the transgene. The examples set forth below show that even more dramatic changes in the number of leaves are possible. Alternatively, the transgenic plant exhibits at least about 10% fewer, more preferably at least about 50% fewer, most preferably at least about 80% fewer leaves at the flower initiation time than the same plant without the transgene. Preferably, the genetically modified plant and the same plant without the transgene are grown under the same conditions.

Plants included in the invention are any plants amenable to transformation techniques, including both monocotyledonous and dicotyledonous plants. Examples of monocotyledonous plants include, but are not limited to, vegetables such as asparagus, onions and garlic; cereals such as maize, barley, wheat, rice, sorghum, pearl millet, rye and oats; and grasses such as forage grasses and turfgrasses. Examples of dicotyledonous plants include, but are not limited to, vegetables, feed, and oil crops such as tomato, beans, soybeans, peppers, lettuce, peas, alfalfa, clover, Brassica species (e.g., cabbage, broccoli, cauliflower, brussel sprouts, rapeseed, and radish), carrot, beets, eggplant, spinach, cucumber, squash, melons, cantaloupe, sunflowers; fiber crops such as cotton; and various ornamentals such as flowers and shrubs.

In another related aspect, the isolated nucleic acid molecules of the present invention can be used to detect and analyze the VIN4 or VIN4-relative gene of a transgenic or non-transgenic plant as an aid to breeding or creating plants having desired flower initiation time.

The above disclosure generally describes the present invention. A more complete understanding can be obtained by reference to the following specific examples which are provided herein for purposes of illustration only and are not intended to limit the scope of the invention.

The complete disclosures of all publications that are cited herein are hereby incorporated by reference as if individually incorporated. It is also understood that, given the limitations of the state of the art, occasional sequence errors or deletions may occur without affecting the usefulness of the data presented. Various modifications and alterations of this invention will become apparent to those skilled in the art without departing from the scope and spirit of this invention, and it should be understood that this invention is not to be unduly limited to the illustrative embodiments set forth herein, but rather is to be construed to be of spirit and scope defined by the appended claims.

EXAMPLES

1. Isolation of the Dominant Late-Flowering Mutant vin4–1D.

In order to identify genes that play a role in the regulation of flower initiation time a population of T-DNA mutagenized lines were created and screened for plants with altered flower initiation time. The T-DNA population was created using an "activation-tagging" vector, pSKI15, containing 4 copies of the Cauliflower mosaic virus 35S enhancer element (Weigel, D., et al., Activation tagging in Arabidopsis. Plant Physiol, 2000. 122(4): p. 1003–13). Insertions of this T-DNA will create both (i) loss-of-function mutations due to gene disruption and (ii) "activation tags" when a phenotype is caused by over or ectopic expression of a gene near the T-DNA insertion site. Activation tags may permit the identification of genes that would not be revealed by loss-of-function mutations due, for example, to redundancy.

We created activation tags in the winter annual type of Arabidopsis. Winter annual types require exposure to cold in order to flower rapidly. The promotion of flowering by cold is known as vernalization. We exposed the activation-tagged lines to cold and screened for mutants that could no longer be vernalized. Table 1 below shows the behavior of an original mutant line vin4–1D. Plants were grown in long day photoperiod conditions (16 hrs light/8 hrs dark). Flower initiation time was measured as the number of leaves formed on the primary stem as well as approximate days to flowering. The wild-type without vernalization flowered with about 75 leaves and after 80 days. This winter annual wildtype flowers rapidly if first vernalized. The vin4–1D mutation delays flowering considerably regardless of whether the mutant plants have been vernalized.

TABLE 1

The vin4-1D mutation blocks flowering in both vernalized and non-vernalized plants.

| Genotype | Number of Leaves on Primary Stem | Approximate Days to Flowering |
| --- | --- | --- |
| Wildtype without vernalization[1] | 74.4 ± 9.8 | 80 days |
| Wildtype with vernalization | 12.8 ± 1.2 | 30 days |
| Vin4-1D without vernalization | >130[2] | >210[2] |
| Vin4-1D with vernalization | >100 | 150 days |

[1]Vernalization is a common procedure to promote flowering in winter annual types of Arabidopsis and other biennial plants. The vernalization procedure is to expose seedlings to 4° C. for 40 days. These 40 days are not counted in the Approximate Days to Flowering column.
[2]Without vernalization, vin4-1D mutants have not flowered after producing more than 130 primary leaves after 210 days.

2. Identification of the VIN4 Gene.

We used the "Adaptor-PCR" method (Siebert, PD., et al., An improved PCR method for walking in uncloned genomic DNA. Nucleic Acid Res., 1995. 23: p. 1087–8) to identify the plant DNA sequence flanking the T-DNA in the vin4–1D mutant. Amplified PCR products were purified and their DNA sequences were determined. Because vin4–1D was a dominant mutant, presumably due to activation, we examined the possible ORFs that were located in a position likely to be activated by the 35S enhancer (i.e. genes located within a few kb of the enhancer). After sequence analysis, one possible ORF (SEQ II) NO:2) was identified by a gene scan program and sequence annotation.

3. Replication of the Late-Flowering Mutant Phenotype by VIN4 overexpression.

To determine (i) whether the ORF mentioned above corresponded to the VIN4 gene and (ii) whether the late-flowering phenotype was due to over-expression of this ORF, we transformed a wild-type summer annual Arabidopsis with a construction (35S:VIN4) in which this ORF is under the control of the constitutive 35S Cauliflower mosaic virus promoter. This construct was sufficient to cause late flowering in Arabidopsis demonstrating that the corresponding ORF did indeed encode VIN4. Table 2 shows flower initiation time of three different individual transformants. The late flowering lines we created by transforming an overexpression construct of VIN4 were late flowering despite being exposed to two stimuli that promote flowering: inductive daylengths (long-day photoperiod conditions) and a flower-promoting cold treatment (vernalization). In other words, overexpression of VIN4 causes delayed flowering in Arabidopsis under a variety of conditions that would otherwise promote flowering. This VIN4 is a general suppressor of flowering for which elevated expression delays flowering regardless of environmental conditions.

TABLE 2

Flowering time of three transgenic lines that contain a 35S::VIN4 construct after exposure to flower-inducing cold and photoperiod treatments.

| | Number of Leaves Formed on Primary Stem | Approximate Days to Flowering |
| --- | --- | --- |
| Wildtype[1] | 9.8 ± 0.5 | 25 days |
| #1 | 34 | 40 days |
| #2 | 45 | 50 days |
| #3 | 80–90 | 120 days |

[1]A summer annual strain of Arabidopsis (Columbia) is the wild type.

4. Identification of VIN4-Relative and Demonstration of the Late-Flowering Phenotype by VIN4-Relative Overexpression.

We identified a second late flowering gene by DNA database search for VIN4 homologs. The second late flowering gene is here named VIN4-relative. The genomic DNA, cDNA and amino acid sequences of VIN4-relative are provided as SEQ ID NOs:4–6, respectively.

Arabidopsis transformants of VIN4-relative were similarly generated as described above for VIN4 transformants using the Cauliflower mosaic virus 35S enhancer element and a genomic fragment that contains VIN4-relative. Three different individual VIN4-relative Arabidopsis transformant lines were analyzed for flower initiation time after exposed to long-day photoperiod conditions. The results are summarized in Table 3.

TABLE 3

Flowering time of three transgenic lines that contain a 35S::VIN4-relative construct after exposure to inductive photoperiods but not to cold.

| | Number of Leaves Formed on Primary Stem | Approximate Days to Flowering |
| --- | --- | --- |
| Wildtype[1] | 9.8 ± 0.5 | 25 days |
| #1 | 25 | 35 days |
| #2 | 25 | 35 days |
| #3 | 45 | 80 days |

[1]The Columbia strain as in Table 2.

We claim:

1. An isolated nucleic acid molecule comprising a polynucleotide or its complement having a nucleotide sequence that encodes a polypeptide, the amino acid sequence of which is identical to SEQ ID NO:3.

2. An isolated nucleic acid molecule comprising a polynucleotide or its complement having a nucleotide sequence identical to SEQ ID NO:2.

3. An isolated nucleic acid molecule comprising:
a polynucleotide, the polynucleotide having a nucleotide sequence that encodes a polypeptide, the polypeptide being identical in amino acid sequence to SEQ ID NO:3, and wherein the polynucleotide is effective when expressed in a transgenic plant to cause a delay in the flower initiation time of the transgenic plant as compared to a non-transgenic plant of the same genetic background; and
a nonnative plant expressible promoter operably linked to the polynucleotide.

4. A constructed nucleic acid molecule comprising:
a polynucleotide, the polynucleotide having an uninterrupted coding sequence that encodes a polypeptide, the polypeptide being identical in amino acid sequence to SEQ ID NO:3, and wherein the polynucleotide is effective when expressed in a transgenic plant to cause a delay in the flower initiation time of the transgenic plant as compared to a non-transgenic plant of the same genetic background; and
a plant expressible promoter operably linked to the polynucleotide.

5. A transgenic plant comprising in its genome the isolated nucleic acid molecule of claim 3.

6. A transgenic plant comprising in its genome the constructed nucleic acid molecule of claim 4.

* * * * *